United States Patent [19]
Ritter

[11] Patent Number: 5,277,900
[45] Date of Patent: Jan. 11, 1994

[54] METHOD FOR BLOOD COAGULATION ON HARD TISSUES

[75] Inventor: Wolfgang Ritter, Hilden, Fed. Rep. of Germany

[73] Assignee: Henkel Kommanditgesellschaft auf Aktien, Duesseldorf, Fed. Rep. of Germany

[21] Appl. No.: 700,351

[22] Filed: Feb. 11, 1985

Related U.S. Application Data

[63] Continuation-in-part of Ser. No. 470,075, Feb. 28, 1983, abandoned.

[30] Foreign Application Priority Data

Aug. 7, 1982 [DE] Fed. Rep. of Germany ....... 3229540

[51] Int. Cl.$^5$ ...................... A61K 31/74; C07C 69/34; C07C 69/52; C07C 69/66
[52] U.S. Cl. .................. 424/78.01; 560/185; 560/198
[58] Field of Search ................... 424/78; 560/198, 185

[56] References Cited

U.S. PATENT DOCUMENTS

| | | | |
|---|---|---|---|
| 2,362,511 | 11/1944 | Teeters | 528/519 |
| 3,496,220 | 2/1970 | McCarty et al. | 560/198 |
| 3,846,479 | 11/1974 | Zech | 560/185 |
| 3,911,098 | 10/1975 | Capozza | 424/19 |
| 3,991,766 | 11/1976 | Schmitt et al. | 424/22 |
| 4,010,196 | 3/1977 | Tsuk | 424/78 |
| 4,011,312 | 3/1977 | Reuter et al. | 424/78 |
| 4,069,381 | 1/1978 | Gaenzler et al. | 560/198 |
| 4,118,470 | 10/1978 | Casey et al. | 424/78 |
| 4,122,129 | 10/1978 | Casey et al. | 424/78 |
| 4,130,639 | 12/1978 | Shalaby et al. | 424/78 |
| 4,393,041 | 7/1983 | Brown et al. | 424/19 |
| 4,563,489 | 1/1986 | Wrist | 424/78 |

OTHER PUBLICATIONS

Douglas, B. L. *Oral Surgery*, vol. 6, p. 1195 (1953).
Selden, H. S., *Oral Surgery*, vol. 29, p. 262 (1970).
Shields, T. W., *Gen'l. Thoracic Surgery*, Lea & Febiger, Phila. (1972).
Wolter, D. et al., *Chirug*, vol. 46, pp. 459-462 (1975).
Geary, I. R. et al., *Ann. Surg.*, vol. 132, p. 1128, (1950).
Howard, C. C. et al., *Clin. Orthop., vol. 63, p. 226 (1969).*
*Merck Index,* 9th ed., alest# 151 & 3735 (1976).

*Primary Examiner*—Dale R. Ore
*Attorney, Agent, or Firm*—Wayne C. Jaeschke; Henry E. Millson; Daniel S. Ortiz

[57] ABSTRACT

A method of using resorbable waxes for coagulation of blood on endogenous hard tissue, especially bone, which waxes consist of waxy polyester-oligomers of hydroxybarboxylic acids which are viscous to solid at body temperature. On the basis of their structure, these waxes are degradable by endogenous metabolic mechanism, wherein the rate of degradation can be adjusted.

25 Claims, No Drawings

METHOD FOR BLOOD COAGULATION ON HARD TISSUES

This application is a continuation-in-part of application Ser. No. 06/470,075, filed Feb. 28, 1983, now abandoned.

BACKGROUND OF THE INVENTION

For mechanical blood coagulation on endogenous hard tissues, for example bone, it is customary to treat resected bone parts with bone wax. For the same reason, blocks of bone wax are also used to cover spaces filled with spongiosa.

The waxy masses used up to the present time were made, for example, of beeswax, almond oil and salicyclic acid, or beeswax and isopropyl palmitate. Relevant literature includes, for example:

Douglas, B. L.: *Oral Surg.*, Vol. 6, p. 1195, 1953;
Selden, H. S.: *Oral Surg.*, Vol. 29, p. 262, 1970;
Shields, T. W.: *General Thoracic Surgery*, Lea and Febiger, Philadelphia, 1972; and
Wolter, D. et al.: *Chirug.*, Vol. 46, p. 459, 1975.

In general, postoperative healing proceeds without disturbance; bacterial contamination is rare.

Commonly, however, in the case of the bone waxes used for coagulation during surgery up to the present time, coverage of the implant by granulation tissue containing abundant macrophages and giant cells is observed, see D. Wolter et al., op cit. The granulation tissue becomes fibrotic within the body with the passage of time.

Direct contact between the bone and the wax does not occur. Nonspecific foreign body reactions often takes place at the spongiosa/bone wax contact zones. This inhibits the new formation of bone and promotes the development of pseudoarthroses, see Geary, I. R. et al.: *Ann. Surg.*, Vol. 132, p. 1128, 1950 and Howard, C. C. et al.: *Clin. Orthop.*, Vol. 63, p. 226, 1969.

DESCRIPTION OF THE INVENTION

The present invention relates to compositions which, because of their consistency, can assume the tasks previously required of a bone wax, but at the same time, as a result of their chemical structure, avoid the disadvantages of the previous bone waxes. In particular, the wax-like compositions in accordance with the present invention are physiologically safe and readily resorbable, and do not lead to the formation of toxic degradation products. In a specific embodiment of the invention, a controllable degradation of these waxy masses by endogenous degradation reactions takes place, so that nonspecific foreign body reactions and, in particular, chronic inflammations at the tissue/bone wax, contact zones is avoided. In addition, as a result of the resorbability of the present compositions in accordance with the invention, uninhibited new formation of bone is promoted.

Thus the object of the invention in a first embodiment, is the preparation and use of resorbable waxes for mechanical blood coagulation on endogenous hard tissue, such as bone, in mammals, especially humans and domesticated animals, wherein these waxes comprise polyester-oligomers of hydroxy carboxylic acids which are highly viscous to solid at mammalian body temperatures. In the prepared embodiment these polyester-oligomers are made of monohydroxy-monocarboxylic acids, although it is also possible for co-reactants to be bound to a corresponding base material of such polyester-oligomers, preferably in a terminal position.

The oligomer segments of these preferred wax compositions contain the structural units:

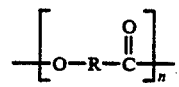

wherein R is a straight or branched chain alkyl group, an unsubstituted or alkyl substituted cycloalkyl group, or an unsubstituted or alkyl substituted phenyl group, with R preferably having from 1 to 20 carbon atoms, more preferably from 2 to 10 carbon atoms, and most preferably from 2 to 6 carbon atoms; and n is an integer dependent on the selection of the R group, and is preferably chosen so that the means molecular weight of the polyester-oligomer chain is in the range of from about 200 to about 1500, more preferably about 300 to about 1000. The desired consistency of wax compositions is attained by careful control of the degree of oligomerization.

The above polyester-oligomer chains are obtained through oligomerization of a hydroxycarboxylic acid, or a mixture of hydroxycarboxylic acids, of the formula

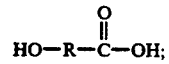

wherein R has the meaning given above.

Especially important hydroxycarboxylic acids for use herein are glycolic acid, the isomeric lactic acids, the possibly isomeric α- or β-hydroxypropionic acids, the possible isomeric α-, β- or γ-hydroxybutyric acids, o-hydroxybenzoic acid (salicylic acid), m-hydroxybenzoic acid and/or p-hydroxybenzoic acid. Specific isomers of the acids mentioned or mixtures of the above can be used. When mixtures of two or more hydroxycarboxylic acids are employed, the R group defined above can have more than one structure in the polyester-oligomer chain, depending on the mixture of hydroxycarboxylic acids chosen for its preparation.

In a particularly preferred embodiment of the invention, the polyester-oligomer is formed essentially from glycolic acid and/or the isomeric lactic acids. By using these reactants in combination it is possible to exert a substantial effect on the degradation rate of the wax by endogenous degradation reactions.

High molecular weight polymers of the type mentioned here and their use in the medical sector are known. They have fiber properties. Their tolerance and degradability have been studied in detail. Well known, for example, are synthetic filament materials, resorbable within the body, based on polyglycolic acid and polylactic acid; see for example U.S. Pat. Nos. 3,297,033; 3,626,948; 2,668,162; 2,676,945 and 2,703,316.

High molecular weight polymeric material of this type have become widely used, for example, for applications in dental medicine, in orthopedics, and for the controlled release of the drugs. They are distinctly superior to comparable natural products, for example, catgut. Extensive data is also available on the degradabilities of these polymers, see especially Miller, R. A. et al.: *J. Biomed., Mat. Res.*, Vol. 11, pp. 711-719, 1977;

Miln, D. C. et al.: *Scot. Med. J.*, Vol. 17, p. 108, 1972; Reed, Am M. et al.: *Polymer,* Vol. 22, p. 494, 1981.

In a known manner using co-condensates of glycolic acid and lactic acid the degradation rate can be adjusted as desired within broad limits; see in this regard the cited publication R. A. Miller et. al.: *J. Biomet., Mat. Res.,* Vol. 11, pp. 711–719, 1977. This information can also be used within the framework of the invention for the compositions of the wax-like polyester-oligomers used in accordance with the invention.

Polyester-oligomers formed from hydroxycarboxylic acids can be manufactured directly by polycondensation of the hydroxycarboxylic acids or hydroxycarboxylic acid mixtures. However, for systematic control of the degree of oligomerization, and thus the desired waxy, highly viscous to solid consistency of the reaction product, it is preferred to regulate the desired degree of oligomerization in a known manner. In this connection it is preferred during the manufacture of the polyester-oligomers to use molecular weight regulating co-reactants; alcohols, carboxylic acids and/or amines are preferred for use in this connection.

Suitable co-reactants include monohydroxy alcohols, monocarboxylic acids or monofunctional amines; however, polyfunctional compounds, especially dihydroxy alcohols or dicarboxylic acids can also be used. In all instances it is possible to regulate the means molecular weight in the polyester-oligomer in a known manner and thus adjust the desired viscosity range for the bone wax in accordance with the invention.

Practically no restriction are imposed on the selection of the monofunctional or difunctional reactants, which, as a rule, are used only in minor quantities. These reactants can be based on saturated or olefinically unsaturated aliphatic or cycloaliphatic groups, or they can be aromatic in nature, e.g. phenyl or alkyl substituted phenyl. In general they have a number of carbon atoms not exceeding $C_{25}$, preferably not exceeding $C_{15}$. Suitable diols contain for example, 2–20 carbon atoms, preferably 2–10, and more preferably 2–6 carbon atoms in the molecules. These same statements re carbon atoms are also applicable to the corresponding dicarboxylic acids. The numerical values for carbon atoms given above, are likewise applicable for the monofunctional alcohols and carboxylic acids.

Examples of suitable diols are:

Ethylene glycol, diethylene glycol, triethylene glycol, tetraethylene glycol, propylene glycol, dipropylene glycol, 1,3-butylene glycol, 1,4-butylene glycol, 2,2-dimethyl-1,3-propanediol, 2,2,4-trimethyl-1,6-hexanediol, 1,4-cyclohexanedimethanol, 1,5-pentanediol, 1,6-hexanediol, 1,10-decanediol and 2,2-bis-(4-hydroxycyclohexyl)-propane.

Examples of dicarboxylic acids that can be employed include: oxalic acid, malonic acid, succinic acid, glutaric acid, adipic acid, pimelic acid, suberic acid, azelaic acid, sebacic acid, isosebacic acid, nonanedicarboxylic acid, decanedicarboxylic acid, undecanedicarboxylic acid, dodecanedicarboxylic acid, phthalic acid, hexahydrophthalic acid, isophthalic acid, terephthalic acid and bipheynyldicarboxylic acid.

Corresponding aliphatic, cycloaliphatic or aromatic monoalcohols, corresponding monocarboxylic acids, and corresponding amines, especially primary or secondary amines, can be used as monovalent co-reactants.

In all instances—both with respect to the hydroxycarboxylic acids and with respect to the co-reactants—not only the respective free reactive components of the types mentioned above can be employed herein, but also their reactive derivatives which under conditions of esterification or ester exchange form the polyester-oligomers of predetermined molecular weight. Thus the esters of hydroxycarboxylic acids are suitable, as well as lactones and lactams of hydroxycarboxylic acids, which can be reacted with diols or diol esters which are subject to ester exchange. The preparation of the polyester-oligomers takes place according to generally known processes, for example, by reaction in the presence or absence of solvents, and if desired in the presence of catalysts, especially esterification catalysts.

If oligomers of the present type are produced by cocondensation of hydroxybarboxylic acids and diols, polyesteroligomers with terminal hydroxyl groups ultimately form. The quantities of diols used, together with the reaction conditions, determine the means molecular weight of the polyester-oligomers obtained. On the other hand, if the oligomers are produced by co-condensation of hydroxycarboxylic acids with dicarboxylic acids or reactive dicarboxylic acid derivatives, polyester-oligomers with terminal carboxyl groups or carboxyl group derivatives are formed. Here also the co-reactant which is also used simultaneously exerts a standardizing effect with regard to the terminal reactive groups as well as a molecular weight regulating effect. Specifically, known technology relating to the manufacture of polyesters or co-polyesters is also applicable here. The simultaneous use of monoalcohols and/or monoamines leads to the desired blockage of the terminal carboxyl acid group in the polyester-oligomer, and correspondingly, the simultaneous use of monocarboxylic acids blocks the terminal hydroxyl group side of the oligomer.

In a preferred embodiment of the invention the bone waxes described herein are solid at mammalian body temperature, i.e., in the temperature range of from about 35° to 40° C. Their mechanical consistency can be selected such that they can be spread in a pasty or soft manner within this temperature range in order to optimally fulfill the purpose for which they are used. However, also suitable are polyester-oligomers which are relatively firm and hard in the range of mammalian body temperature, and which can be brought into a pasty to soft spreadable condition by moderate heating.

When applying the waxes of the invention to the mammalian body, only very small quantities of the bone wax are needed to block off a blood vessel. These quantities can, for example, be brought into the desired pasty condition by slightly preheating on a spatula and used in this form, whereupon they harden into a solid occlusion material in the range of body temperature. Suitable, for example, are corresponding waxes which develop the desired degree of soft workability at temperatures up to about 100° C., preferably up to about 60° C.

The following examples are given for illustration purposes only and not to limit the invention.

EXAMPLES 1 α 3

Glycolic acid and ethylene glycol are placed in a three-necked flask with stirrer and distillation bridge. They are rapidly heated to 150° C. under nitrogen, and then from 150° to 200° C. in the course of 6 hours. Most of the water of reaction, which indicates the occurrence of ester condensation, splits off at this time. The batch is permitted to cool to about 150° C., evacuated cautiously to 10 Torr, and the reaction completed at 200° C. and 10 Torr. After 30 minutes the product is removed in the hot state at about 150° C. The composition of the batches and the oligomers properties are shown in Table 1 below.

TABLE 1

OLIGOHYDROXYCARBOXYLIC ACIDS FROM GLYCOLIC ACID AND ETHYLENE GLYCOL

| Example | Adducts | | Yield of reaction water, % | Appearance |
|---|---|---|---|---|
| | Glycolic acid, moles | ethylene glycol, moles | | |
| 1 | 3 | 1 | 100 | clear, viscous, light yellow |
| 2 | 4 | 1 | 90 | viscous, white |
| 3 | 6 | 1 | 98 | waxy, white |

EXAMPLES 4–8

In a three-necked flask equipped with stirrer and distillation bridge, glycolic acid and adipic acid are placed. Heating is rapidly carried out to 150° C. under nitrogen, and then within 6 hours, from 150° and 200° C. At this time most of the reaction water has already split off, indicating occurrence of the ester condensation. The batch is permitted to cool to about 150° C., carefully evacuated to 10 Torr, and the reaction completed at 200° C. and 10 Torr. The product is removed while not hot under nitrogen. The composition of the batch and the oligomer properties are given in Table 2 below.

TABLE 2

OLIGOHYDROXYCARBOXYLIC ACIDS FROM GLYCOLIC ACID AND ADIPIC ACID

| Example | Adducts | | Yield of reaction water, % | Appearance |
|---|---|---|---|---|
| | glycolic acid, moles | adipic acid, moles | | |
| 4 | 1 | 1 | 99 | waxy, solid |
| 5 | 2 | 1 | 99 | waxy |
| 6 | 3 | 1 | 98 | waxy, soft |
| 7 | 4 | 1 | 96 | waxy, soft |
| 8 | 6 | 1 | 98 | waxy, soft |

EXAMPLE 9

In a surgical procedure in a human patient for the repair of a compound fracture of a fibula by resection of a portion thereof, a small quantity of the oligohydorxycarboxylic acid prepared in EXAMPLE 6 is applied to the resected bone. Bleeding in the area is quickly and effectively controlled when the resected bone is implanted.

During a period of several months following completion of the surgical procedure, the oligohydroxycarboxylic acid is slowly and completely resorbed by the body, without any deleterious side effects. No noticeable interference with new bone formation occurs from use of this bone wax.

CLARIFICATION OF DESCRIPTION AND SUPPLEMENTAL EXAMPLES

The following material has been added by the filing of this continuation-in-part application, while the preceeding disclosure is essentially unchanged from the parent application. The Clarification section is believed to be either specifically or inherently disclosed in the preceeding disclosure.

1. CLARIFICATION OF DESCRIPTION

Many oligomers from $C_{2-10}$ monohydroxycarboxylic acids are already known. Products of this type, at least insofar as they have been a certain molecular weight and are solid, have already been used in medicine. Numerous possibilities for use have been suggested. These are listed by way of example in U.S. Pat. No. 3,991,766 (Schmitt) at columns 3 and 4.

The present invention provides a method for using such products for blood coagulation in hard body tissues, especially bones.

Only bees' wax has been used for this purpose to date, although this substance is not degradable, remains at the affected point in the body, and can produce harmful side effects. From the literature reference of Douglas, Oral Surg., Vol. 6, p. 1195, (1953), it is apparent that a demand for degradable bone waxes already existed in 1953. However up to the present time this problem has not been solved, so that the present invention suggests a practical solution for the first time.

Waxy polyester-oligomers of at least one hydroxy carboxylic acid are suitable for the purposes of this invention. This general concept covers the following products:

a) Oligomers with carboxyl end groups prepared from hydroxy carboxylic acids, their lactones (lactide or glycolite for example) and dicarboxylic acids.

b) Oligomers with hydroxyl end groups prepared from hydroxy carboxylic acids and/or their lactones and dihydroxy compounds, for example ethylene glycol.

c) Oligomers with only one hydroxy or carboxyl end group prepared from hydroxy carboxylic acids and/or their lactones and monofunctional carboxylic acids or monofunctional alcohols.

d) Oligomers with both hydroxyl and carboxyl end groups prepared from hydroxy carboxylic acids and/or their lactones under termination of the esterification reaction after reaching a partial conversion degree selected at will.

The following can be stated regarding the molecular weight of such products:

In the case of polycondensates of this type the molecular weight can be simply calculated from the components. For this purpose one first calculates the number of mols of hydroxy carboxylic acid used per mol of regulator such as dicarboxylic acid in above product a), dihydroxy compound in above product b), etc. This number is multiplied by the molecular weight of the monomeric hydroxy carboxylic acid minus 18, and the molecular weight of the regulator is added to it. In this manner one can also derive accurate molecular weights from the statements of the preceeding original disclosure, i.e., from Examples 1–8. In the case of the above product d) the molecular weight following conversion can be calculated. For further details the reader is referred to: W. H. Carothers, et al., *J. Am. Chem. So.*, Vol. 51, p. 2548, (1929) as well as P. J. Flory, *Principles of Polymer Chemistry*, Cornell University Press, New York, (1953).

The molecular weights that can be calculated in this way or can be determined via end group determinations are number averages (Mn).

The products in accordance with the invention to some extent have a chemical coagulating effect in addition to the previously known and described mechanical blood coagulating effect. Experiments with bovine blood have revealed that oligomers containing glycolic acid as building blocks lead to coagulation of bovine blood on the contact surface. This is a property which is inherent in the method of the parent application, particularly from Example 9. It may therefore be considered as merely a further description and clarification of the manner in which the originally disclosed invention operates.

EXAMPLES S8-S23

The following examples were produced according to the procedures of Examples 1 to 3 of the preceeding disclosure, only the reaction products of ethyl lactate with glycol or glycerine were catalyzed with sodium methylate (100 mg/mol ethyl lactate). The customary reaction times were 15 hr. The parameters and results are given in Table 4.

TABLE 4

| Example No. | Hydroxycarboxylic acid | Regulator | Molar ratio | Molecular weight (theoretical) | Viscosity | Color |
| --- | --- | --- | --- | --- | --- | --- |
| S8 | glycolic acid | ethylene glycol | 3:1 | 236 | liquid-viscous | colorless |
| S9 | glycolic acid | ethylene glycol | 4:1 | 294 | viscous | yellowish |
| S10 | glycolic acid | ethylene glycol | 6:1 | 410 | pasty | white |
| S11 | ethyl lactate | ethylene glycol | 2:1 | 206 | fluid | yellow |
| S12 | ethyl lactate | ethylene glycol | 4:1 | 351 | slighly viscous | dark |
| S13 | ethyl lactate | ethylene glycol | 6:1 | 495 | viscous | dark |
| S14 | ethyl lactate | ethylene glycol | 10:1 | 787 | viscous | dark |
| S15 | glycolic acid ethyl lactate | ethylene glycol | 5:1:1 | 424 | viscous | yellowish |
| S16 | glycolic acid ethyl lactate | ethylene glycol | 4:2:1 | 438 | highly viscous | slightly yellowish |
| S17 | glycolic acid ethyl lactate | ethylene glycol | 10:2:1 | 786 | pasty | yellowish |
| S18 | glycolic acid ethyl lactate | ethylene glycol | 8:4:1 | 815 | pasty partially crystalline | yellowish |
| S19 | glycolic acid | glycerine | 3:1 | 266 | highly viscous | yellowish |
| S20 | glycolic acid | glycerine | 6:1 | 440 | highly viscous pasty | yellowish |
| S21 | ethyl lactate | glycerine | 6:1 | 525 | viscous | dark |
| S22 | ethyl lactate | glycerine | 12:1 | 957 | highly viscous | dark |
| S23 | glycolic acid ethyl lactate | glycerine | 5:1:1 | 454 | highly viscous | yellow |

2. SUPPLEMENTAL EXAMPLES

EXAMPLES S1-S7

Preparation of oligomers with two hydroxyl end groups by reaction of lactide (internal ester of two molecules of lactic acid) with ethylene glycol.
Procedure:

The predetermined quantity of lactide and the dihydroxy compound were heated in a conventional laboratory apparatus under nitrogen and under agitation to 195° C. within 1 hr. Then they were permitted to react for 3 hr at 195° C. and transfered in the hot state. An SN II chloride solution in ether was present as a catalyst (7 ml of a solution of 2.5 g $SNCl_2$ in 1000 ml ether in the reaction of 3 moles lactide with 1 mole ethylene glycol).

The reaction ingredients and results are given in Table 3.

EXAMPLE S24

The effect of the substances on bovine blood was tested in an in vitro experiment. For this purpose a thin layer of the oligomers of each of Examples S8-S23 was spread onto dry wood, and two drops of bovine blood were placed on the product. On the oligomers which contained no glycolic acid component no discoloration or coagulation could be observed even after 15 min. The oligomers which contained glycolic acid caused darkening after only 40 to 100 sec and produced complete coagulation after a maximum of 15 min.

I claim:

1. A method for blood coagulation on endogenous hard body tissues, comprising:
   - applying to said hard body tissues a blood-coagulation effective amount of at least one polyesteroligomer of at least one hydroxycarboxylic acid,

TABLE 3

| Example No. | Mols lactide | Mols ethylene glycol | Molecular weight (Mn) (theoretical) | OH-No. measured | Viscosity according to Brookfield (Pas) | Spindle no. | Rotation rate (min[1]) | Water solubility | Fluidity |
| --- | --- | --- | --- | --- | --- | --- | --- | --- | --- |
| S1 | 1.5 | 1 | 278 | 386 | 0.88 | 5 | 50 | + | + |
| S2 | 3.0 | 1 | 494 | 191 | 50 | 7 | 10 | − | + |
| S3 | 6.0 | 1 | 926 | 89.3 | 8000 | 7 | 0.5 | − | − |
| S4 | 12.0 | 1 | 1790 | 45.6 | >8000 | 7 | 0.5 | − | − |
| S5 | 1.5 | 1 | 308 | 487 | 16.1 | 5 | 20 | + | + |
| S6 | 3 | 1 | 524 | 275 | 720 | 7 | 1 | − | − |
| S7 | 6 | 1 | 956 | 151 | 8000 | 7 | 0.5 | − | − | which is in the form of a wax which is viscous to solid at temperatures of about 35° to 40° C.; and
- permitting said wax to be resorbed by the body which occurs without the formation of toxic degradation products and without nonspecific foreign body reactions.

2. The method of claim 1 wherein said at least one polyester oligomer is a monohydroxy-monocarboxylic acid.

3. The method of claim 1 wherein said at least one polyester oligomer is a monohydroxy-monocarboxylic acid having a co-reactant bound thereto in a terminal position.

4. The method of claim 1 wherein each of said at least one polyester-oligomer contains the repeating structural unit:

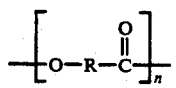

wherein
R is—a straight or branched chain alkyl; or an unsubstituted or alkyl substituted phenyl; with the proviso that R has 1 to 20 carbon atoms; and
n is—an integer dependent on the selection of R and is chosen so that the number average molecular weight of said oligomer is about 200 to 1,500.

5. The method of claim 4 wherein n is chosen so that the number average molecular weight of said oligomer is about 300 to 1,000.

6. The method of claim 1 wherein said wax is a solid whose mechanical consistency permits spreading within said temperature range of about 35° to 40° C.

7. The method of claim 1 wherein said wax is a solid which softens to a mechanical consistency which permits spreading, when heated to a temperature up to about 100° C.

8. The method of claim 1 wherein said wax is a solid which softens to a mechanical consistency which permits spreading, when heated to a temperature up to about 60° C.

9. The method of claim 4 wherein R has 2 to 10 carbon atoms.

10. The method of claim 4 wherein R has 2 to 6 carbon atoms.

11. The method of claim 1 wherein said hydroxycarboxylic acid is at least one of: glycolic, lactic, hydroxypropionic, hydroxybutyric, or hydroxybenzoic acids.

12. The method of claim 1 wherein said polyesteroligomer has at least one co-reactant moiety bound thereto in a terminal position, said co-reactant being: a monohydroxy alcohol; a dihydroxy alcohol; a monocarboxylic acid; a dicarboxylic acid; a primary monoamine; or a secondary monoamine; said co-reactant having not more than 25 carbon atoms.

13. The method of claim 12 wherein said co-reactant has not more than 15 carbon atoms.

14. The method of claim 1 wherein said hydroxycarboxylic acid is glycolic acid.

15. The method of claim 12 wherein said hydroxycarboxylic acid is glycolic acid.

16. The method of claim 15 wherein said co-reactant is ethylene glycol.

17. The method of claim 16 wherein the mol ratio of glycolic acid to ethylene glycol is 3:1.

18. The method of claim 16 wherein the mol ratio of glycolic acid to ethylene glycol is 4:1.

19. The method of claim 16 wherein the mol ratio of glycolic acid to ethylene glycol is 6:1.

20. The method of claim 15 wherein said co-reactant is adipic acid.

21. The method of claim 20 wherein the mol ratio of glycolic acid to adipic acid is 1:1.

22. The method of claim 20 wherein the mol ratio of glycolic acid to adipic acid is 2:1.

23. The method of claim 20 wherein the mol ratio of glycolic acid to adipic acid is 3:1.

24. The method of claim 20 wherein the mol ratio of glycolic acid to adipic acid is 4:1.

25. The method of claim 20 wherein the mol ratio of glycolic acid to adipic acid is 6:1.

* * * * *